United States Patent [19]

Harvey, Sr. et al.

[11] E Patent Number: Re. 32,972

[45] Reissued Date of Patent: Jul. 4, 1989

[54] PERMANENT DENTAL PROSTHESIS AND METHOD

[76] Inventors: Arthur E. Harvey, Sr., Davis Ave., R.D. #2, Pawcatuck, Conn. 06379; Thomas J. Harvey, 64 Floral Park Blvd., Pawtucket, R.I. 02861

[21] Appl. No.: 168,006

[22] Filed: Mar. 3, 1988

Related U.S. Patent Documents

Reissue of:

[64] Patent No.: 4,661,067
Issued: Apr. 28, 1987
Appl. No.: 832,769
Filed: Feb. 24, 1986

[51] Int. Cl.[4] ..... A61C 13/12

[52] U.S. Cl. ..... 433/181; 433/180; 433/182

[58] Field of Search ..... 433/180, 181, 182, 183, 433/172, 177

[56] References Cited

U.S. PATENT DOCUMENTS

| | | | |
|---|---|---|---|
| 3,717,931 | 2/1973 | Konig | 433/177 |
| 4,163,318 | 8/1979 | Tigani | 433/172 |
| 4,302,187 | 11/1981 | Yoon | 433/177 |
| 4,345,901 | 8/1982 | Romagnoli | 433/172 |
| 4,348,181 | 9/1982 | Dawson | 433/172 |
| 4,380,434 | 4/1983 | Weissman | 433/177 |
| 4,406,622 | 9/1983 | Yoon | 433/172 |
| 4,431,415 | 2/1984 | Tigani | 433/172 |
| 4,583,948 | 4/1986 | Jansen | 433/181 |
| 4,609,355 | 9/1986 | Harvey, Sr. et al. | 433/177 |

*Primary Examiner*—Gene Mancene
*Assistant Examiner*—Adriene J. Lepiane
*Attorney, Agent, or Firm*—Salter & Michaelson

[57] ABSTRACT

A base structure for a dental prosthesis comprises first and second anchor elements which are permanently securable to the teeth on opposite sides of a space or gap in the tooth structure of a patient and a base element which is securable to the anchor elements in the gap but which comprises slidably interfitted first and second base element portions so that it is expandable to fit the width of the gap. The method of securing and forming a dental prosthesis in the gap with the base structure comprises the steps of securing the anchor elements on the teeth on opposite sides of the gap, assembling the base element with the anchor elements in the gap, securing the first and second base element portions together, forming an outer shell on the base element and securing the base element with the outer shell thereon to the anchor elements.

16 Claims, 2 Drawing Sheets

PERMANENT DENTAL PROSTHESIS AND METHOD

Matter enclosed in heavy brackets [ ] appears in the original patent but forms no part of this reissue specification; matter printed in italics indicates the additions made by reissue.

BACKGROUND AND SUMMARY OF THE INVENTION

The instant invention relates to the field of dentistry, and more particularly to an improved base structure for a dental prosthesis and to a method of installing and assembling the prosthesis in the mouth of a patient.

A variety of different types of removable and permanent dental prostheses have been heretofore available for replacing missing teeth in the mouths of patients. In this connection, conventional removable dental bridges possibly represent the most common type of heretofore available dental prosthesis, and they have been utilized for replacing missing teeth in mouths of patients for many years. Other types of heretofore-available removable dental prostheses are disclosed in the U.S. Pat. Nos. 1,685,289 to Miller; 1,702,282 Stoloff; 3,717,931 Konig; 4,302,187 Yoon; 4,345,901 Romagnoli; 4,348,181 Dawson; 4,380,434 Weissman; and 4,406,622 Yoon. More recently, however, it has been recognized that it is possible to permanently secure a dental prosthesis in the mouth of a patient to provide a permanent replacement for one or more missing teeth and that a permanent prosthesis can have significant advantages over a removable prosthesis from a practical standpoint. The device disclosed in the U.S. Pat. No. 4,163,318 to Tigani which represents the closest prior art to the instant invention of which the applicants are aware and the device disclosed in the applicants' copending U.S. pat. application Ser. No. 751,371 now U.S. Pat. No. 4,609,355 issued on 9/02/86 are generally exemplary of some of the types of permanent dental prostheses which have been heretofore known. Generally, the heretofore known permanent dental prostheses have comprised a body portion which defines an artificial tooth or at least a base structure for an artificial tooth and a pair of pins or tabs which extend outwardly from opposite sides of the body portion and are receivable in notches or holes in the adjacent natural teeth for securing the body portion between the two natural teeth. In most cases, the pins or tabs of a prostheses of this type have beem cemented in the holes or notches in the adjacent teeth to secure the body portion of the prosthesis in position. As an alternative to this type of structure, another type of permanent dental prosthesis has recently been developed comprising anchor elements which are permanently securable to the sides of the teeth on either side of an opening or gap in the mouth of a patient and a body portion which is permanently securable to the anchor elements to secure it in the gap. In this connection, the anchor elements which are used in a prosthesis of this type are permanently securable to the adjacent teeth with pins which are cemented in small holes in the adjacent teeth, Until recently, it was not practical to secure anchor elements in this manner since it was extremely difficult to drill the proper holes with the types of dental drills which are available. However, recent improvements in dental drills have now made the use of anchor elements of this type practical. In any event, it has been found that anchor elements which are permanently secured to teeth in this manner can provide an effective and durable means of securing a dental prosthesis in the mouth of a patient. Nevertheless, although anchor elements of this type have recently been used for securing artificial teeth in the mouths of patients, they have only been used in combination with preformed artificial teeth which have not been adjustable to fit gaps of different sizes and which have therefore required substantial amounts of custom dental work in order to adapt and fit them to the mouths of patients and in order to adapt them to be secured with anchor elements.

The instant invention provides a novel and effective base structure for a dental prosthesis which is securable in the mouth of a patient with anchor elements of the above-described type but which is adjustable to adapt it to be installed in the mouth of a patient without substantial amounts of custom dental laboratory work. Specifically, the base structure for a dental prosthesis of the instant invention comprises first and second anchor elements which are securable on the sides of spaced first and second teeth and a base element which is securable to the anchor elements to retain the base element in the gap between the first and second teeth. The base element, however, comprises first and second base element portions which are received in interfitting relation and slidable in telescoping relation with respect to each other in a direction which extends between the anchor elements to enable the base element to be adjusted to fit the width of the gap. The anchor elements are preferably tapered in their outward extents away from the gum of the patient when they are mounted on their respective teeth, and the base element is configured to receive the first and second anchor elements in snug, interfitting relation when the base element is aligned with the gap and advanced toward the gum. The first and second base element portions preferably define a tooth-like configuration of slightly reduced dimension in the base element, the first base element portion preferably has an aperture therein which is disposed in a direction which extends between the anchor elements, and the second base element portion preferably comprises a pin which is slidably received in the aperture in the first base element portion to enable the first and second base element portions to be slidably adjusted in telescoping relation with respect to each other. Further, the pin in the second base element portion is preferably received in the aperture in the first base element portion so that the first and second base element portions are slightly rotatable with respect to each other to compensate for minor misalignments in the positions of the anchor elements on the adjacent teeth and in one embodiment of the base structure, a spring is provided for biasing the first and second base element portions apart.

In order to secure and form a dental prosthesis in the mouth of a patient in accordance with the method of the instant invention, first and second anchor elements are secured to spaced first and second teeth, respectively, on opposite sides of a gap in the mouth of a patient, and the base element is assembled in the gap so that it is received in interfitting relation with the anchor elements. In this regard, because the first and second base element portions are slidable with respect to each other and preferably slightly rotatable, they can easily be interfitted and assembled with the anchor elements without requiring custom dental laboratory work. After the base element has been assembled with the anchor elements in the gap in this manner, the first and second base element portions are permanently secured with respect to each other, and an outer shell or casing having a tooth-like outer configuration is formed over the base element. Thereafter, the base element with the outer casing thereon is secured to the anchor elements to provide a permanently secured prosthesis in the mouth of the patient. In the preferred application of the method, after the anchor elements have been secured on the first and second teeth in the mouth of the patient but before the base element has been assembled in the gap, a study model is made of the first and second teeth with the anchor elements thereon by conventional dental techniques. The base element is then assembled with the anchor elements in the gap and the first and second base element portions are cemented together. Thereafter, the base element is removed from the patient's mouth and placed on the study model, the outer shell is formed on the base element while it is on the study model, and finally the base element with the outer shell thereon is installed in the mouth of the patient and secured to the anchor elements with a suitable cement.

Accordingly, it is a primary object of the instant invention to provide an effective base structure for a permanent dental prosthesis.

Another object of the instant invention is to provide a dental prosthesis comprising an adjustable base element and a pair of anchor elements which are securable to a pair of spaced teeth in the mouth of a patient.

A still further object of the instant invention is to provide an improved method of forming and securing one or more artificial teeth in the mouth of a patient.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
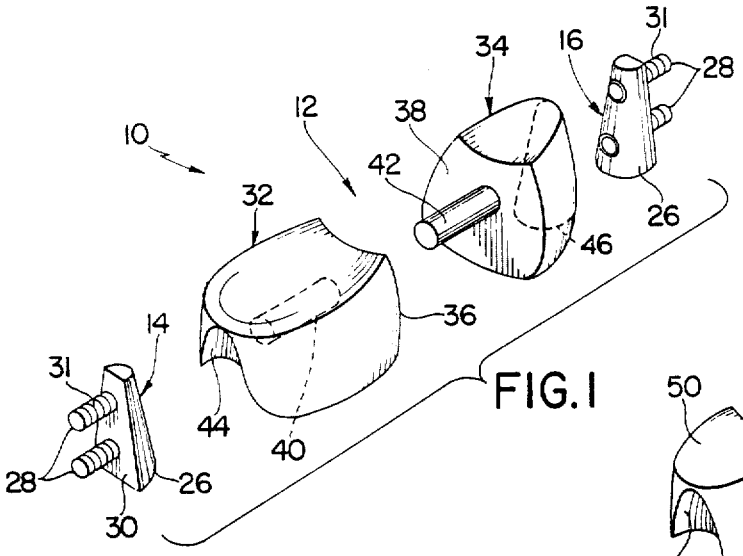
FIG. 1 is an enlarged exploded perspective view of the base structure of the instant invention.
Figure 2:
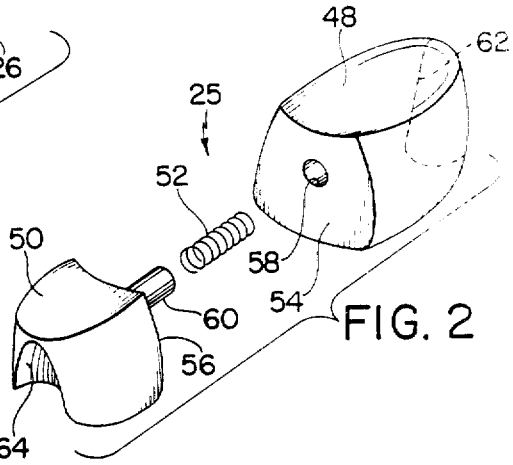
FIG. 2 is an enlarged exploded perspective view of the base element of a second embodiment of the base structure.
Figure 3:
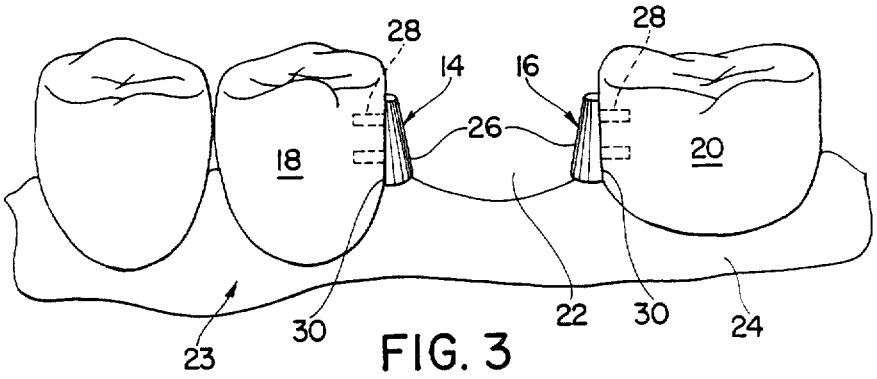
FIG. 3 is an enlarged fragmentary elevational view of the jaw and tooth structure of a patient with a pair of anchor elements assembled on a pair of the teeth thereof.
Figure 4:
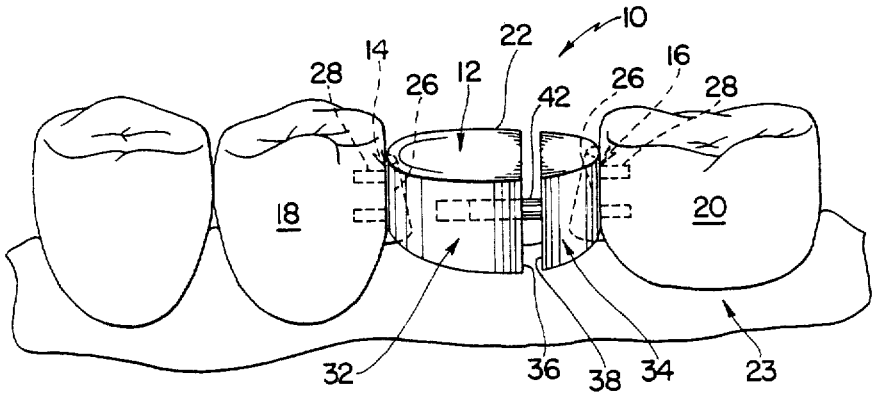
FIG. 4 is a similar view with the base element assembled with the anchor elements.
Figure 5:
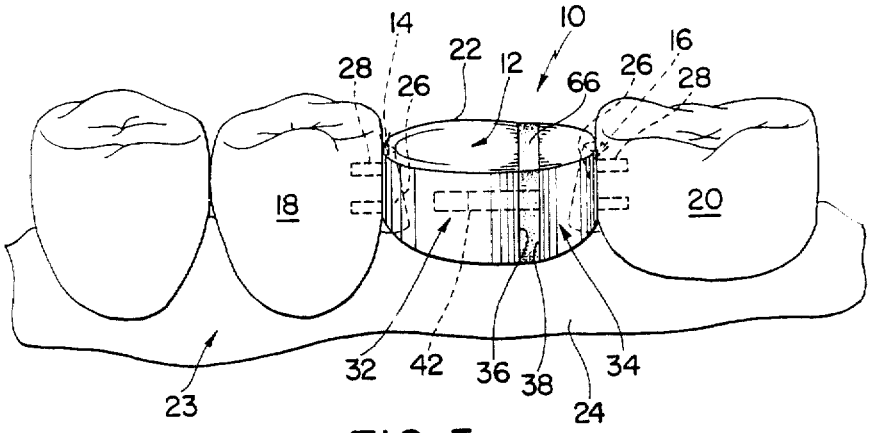
FIG. 5 is a similar view with the first and second portions of the base element secured together.

Referring now to the drawings, a first embodiment of the base structure of the instant invention is illustrated in FIGS. 1, 4 and 5 and generally indicated at 10. The base structure 10 comprises a base element generally indicated at 12 and first and second anchor elements generally indicated at 14 and 16, respectively, in FIGS. 1 and 3 which are receivable in assembled relation with the base element 12 for securing it in the mouth of a patient. More specifically, the anchor elements 14 and 16 are securable on first and second teeth 18 and 20 which define a gap 22 therebetween and which are mounted on a gum structure 23 comprising a gum 24. When the anchor elements 14 and 16 are mounted in this manner, the base element 12 is receivable in the gap 22 for providing a rugged and durable base structure for a permanent dental prosthesis comprising one or more artificial teeth. A base element of a second embodiment of the base structure of the instant invention is illustrated and generally indicated at 25 in FIG. 2, and it is adapted to be mounted in a similar manner on similar anchor elements in a similar gap.

The anchor elements 14 and 16 are preferably of conventional construction and preferably made of a suitable corrosion-resistant metal which is suitable for dental applications, such as stainless steel, and the anchor elements 14 and 16 each comprises a body portion 26 and a pair of spaced pins 28. The body portions 26 are each preferably formed in a generally truncated conical configuration, although they have longitudinally extending flattened sides 30 thereon which are receivable in substantially mating relation with the sides of the teeth 18 or 20 to enable them to be effectively mounted thereon. In addition, the surfaces of the body portions 26 are preferably etched by conventional techniques to make them more receptive to adhesives. The pins 28 are assembled with the body portions 26 so that they project from the flattened sides 30 thereof, and they are preferably formed with spaced annular rings 31 thereon which enable them to be more effectively cemented in holes in the sides of the teeth 18 and 20. It will be understood, however, that while the anchor elements 14 and 16 are herein embodied as having generally truncated conically shaped body portions 26 and as each having two spaced pins 28, it will be understood that the base structures 10 can be effectively constructed with other types of anchor elements having body portions of different configurations and having different quantities of pins 28.

The base element 12 is preferably made of a suitable corrosion-resistant metal which is suitable for dental applications, such as stainless steel, and it comprises first and second base element portions generally indicated at 32 and 34, respectively, which preferably cooperate to define a reduced tooth-like configuration in the base element 12 and which are preferably etched on the surfaces thereof to make them more receptive to adhesives, composite filler materials, etc. The base element portions 32 and 34 have inner mating surfaces 36 and 38, respectively, which are receivable in substantially mating relation, a bore 40 is formed and positioned in the first base element portion 32 so that it extends inwardly from the inner mating surface 36 thereon, and a pin 42 is formed and positioned in the second base element portion 34 so that it projects outwardly from the inner mating surface 38 thereon. The bore 40 and the pin 42 are positioned on their respective base element portions 32 and 34 so that the pin 42 is slidably receivable in the bore 40 and so that the bore 40 and the pin 42 cooperate for retaining the first and second base element portions 32 and 34, respectively, in generally aligned relation. Accordingly, when the pin 42 is entirely received in the bore 40, the mating surfaces 36, 38 are preferably received in mating engagement, although the first and second base element portions 32 and 34, respectively, are preferably at least slightly rotatable with respect to each other to compensate for slight misalignments in the positions of the anchor elements 14 and 16. Formed on the sides of the first and second base element portions 32 and 34 which face generally away or opposite from the mating surfaces 36 and 38 thereof, respectively, are first and second notches 44 and 46, respectively, which are dimensioned and configured to receive the first and second anchor elements 14 and 16, respectively. More specifically, the notches 44 and 46 are preferably formed in generally open-sided truncated conical configurations, and they are oriented to receive the anchor elements 14 and 16, respectively, when the base element 10 is generally aligned with the gap 22 and advanced therein toward the gum 24. Further, since the pin 42 is slidable in telescoping relation in the bore 40, the width of the base element 12 is automatically adjusted to fit the width of the gap 22 when the base element 12 is assembled with the anchor elements 14 and 16 in this manner.

The base element 25 is similar to the base element 12, it is made of a suitable metal, and it includes first and second base element portions 48 and 50, respectively, which are preferably etched on the surfaces thereof, and a resilient spring 52. The base element portions 48 and 50 have mating surfaces 54 and 56 thereon, respectively, and a bore 58 extends inwardly from the mating surface 54 on the first base element portion 48, whereas a pin 60 projects outwardly from the mating surface 56 on the second base element portion 50. The bore 58 extends partially through the first base element portion 48, the spring 52 is received in the bore 58, and the pin 60 is slidably received in the bore 58, so that the spring element 52 biases the first and second base element portions 48 and 50 apart. Formed on the outer sides of the first and second base element portions 48 and 50 which face generally opposite or away from the mating surfaces 54 and 56 thereof are notches 62 and 64 which are dimensioned and configured to receive the anchor elements 14 and 16, respectively, in interfitting assembled relation for securing the base element 25 in the gap 22.

Figure 6:
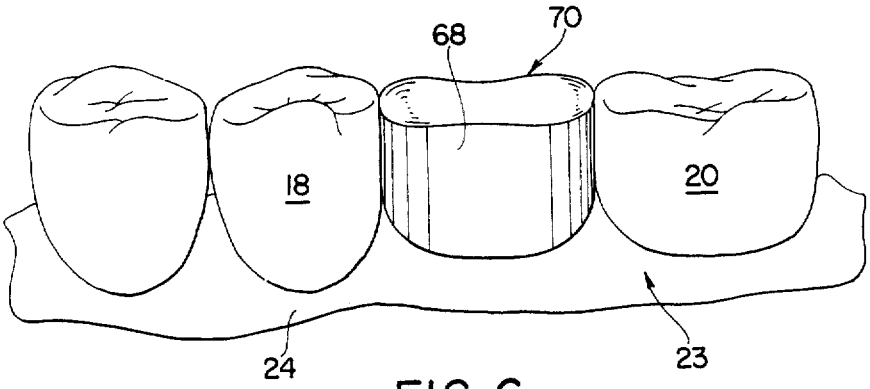
FIG. 6 is a similar view with the outer casing assembled on the base structure.

The method of the instant invention can be effectively applied to form and assemble a permanent dental prosthesis in the mouth of a patient which includes a base element such as the base element 10 or the base element 25. In this regard, the method of the instant invention is herein described as it is applied with the base element 12, although it will be understood that the base element 25 could also be installed in accordance with the method to form an effective dental prosthesis. In the first step of the method of the instant invention as herein embodied, the anchor elements 14 and 16 are permanently installed on the teeth 18 and 20 in the gap 22. The anchor elements 14 and 16 are preferably installed in a conventional manner by first drilling small holes in the sides of the teeth 18 and 20 which face the gap 22 and by then cementing the anchor elements 14 and 16 to the teeth 18 and 20, respectively, so that the pins 28 on the anchor elements 14 and 16 extend into the drill holes in the teeth 18 and 20. In this regard, the portions of the teeth 18 and 20 which face the surfaces 30 on the anchor elements 14 and 16 are preferably etched before the anchor elements 14 and 16 are cemented to the teeth 18 and 20 to provide effective bonding surfaces for the anchor elements 14 and 16, and thereafter the anchor elements 14 and 16 are preferably cemented to the teeth 18 and 20 with an effective and durable dental cement, such as a glass cement ionomer or a resin cement. After the anchor elements 14 and 16 have been permanently secured to the teeth 18 and 20 in this manner, a study model of the teeth 18 and 20 with the anchor elements 14 and 16 thereon is preferably made in a conventional manner so that a portion of the remainder of the method can be effected outside of the mouth of the patient. In any event, after the anchor elements 14 and 16 have been assembled on the teeth 18 and 20, respectively, the base element 12 is assembled with the anchor elements 14 and 16 in the gap 22. This is carried out by positioning the base element 12 so that it is aligned with the gap 22 and so that the first and second notches 44 and 46 are aligned with the first and second anchor elements 14 and 16, respectively, and by thereafter advancing the base element 12 toward the gum 24 in the gap 22 so that it is positioned in the manner illustrated in FIG. 4. In this regard, since the pin 42 is slidable in telescoping relation in the bore 40, the width of the base element 12 is automatically adjusted to fit the width of the gap 22 by aligning the notches 44 and 46 with the anchor elements 14 and 16, respectively. Further, because of the rounded configurations of the anchor elements 14 and 16 and the notches 44 and 46, and because the base element portions 32 and 34 are slidably interfitted and at least slightly rotatable with respect to each other, the base element 12 can effectively compensate for minor misalignments between the teeth 18 and 20, as well as minor misalignments in the positions of the anchor elements 14 and 16 thereon. After the base element 12 has been assembled in the gap 22 in this manner, a cement 66 is applied to the base element portions 32 and 34, as illustrated in FIG. 5, in order to secure them with respect to each other. This is preferably carried out by utilizing a conventional dental cement or a composite material such as a ceramic composite material, and the entire space between the base element portions 32 and 34 is preferably filled with the cement or composite material to provide a solid structure. Finally, after the cement or composite material 66 has been applied to the base element portions 32 and 34 to permanently secure them together, an outer shell 68 is formed in a tooth-like configuration over the base element 12. This is preferably carried out by first removing the base element 12 from the mouth of the patient and assembling it on the study model and by thereafter applying a ceramic composite material or a ceramic composite material plus a porcelain or acrylic veneer over the base element 12 to provide a tooth-like outer configuration therefor which is customized for the patient to provide an effective artificial tooth, such as the one generally indicated at 70 in FIG. 6. Finally, after the tooth 70 has been fully formed in this manner, it is cemented to the anchor elements 14 and 16 with a permanent cement, such as a glass ionomer cement or a resin cement so that it is permanently secured in the gap 22 in the position illustrated in FIG. 6.

It is seen, therefore, that the instant invention provides an effective base structure for a dental prosthesis and an effective method of assembling and forming a dental prosthesis in the mouth of a patient. The base elements 12 and 25 can be effectively adjusted to fit the widths of gaps in the mouths of patients, and the base elements 12 and 25 can be effectively utilized in the method of the instant invention for forming effective dental prostheses, such as the finished tooth 70. Further, the base elements 12 and 25 can be effectively and permanently supported on the anchor elements 14 and 16 to provide base structures for artificial teeth which are durable and which can be adapted to provide aesthetically pleasing replacement teeth in the mouths of patients. In addition, since the base element of the base structure is adjustable to fit the width of a gap in the mouth of a patient and also to compensate for minor misalignments in the adjacent teeth and the positions of the anchor elements, the entire method can normally be performed in a dentist's office without requiring custom dental lab work. Accordingly, it is seen that the base structure of the instant invention and the method of forming an artificial tooth in accordance with the instant invention represent significant advancements in the dental art which have substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. In a base structure for a dental prosthesis wherein the base structure is of the type which is permanently securable in a gap between spaced first and second teeth in the mouth of a patient and comprises first and second anchor elements securable on said first and second teeth, respectively, in said gap and a base element securable to said first and second anchor elements when they are secured on their respective teeth to retain said base element in a position wherein it extends therebetween, the improvement comprising said base element comprising first and second base element portions which are receivable in interfitting relation with said first and second anchor elements, respectively, so that they are nonrotatable relative to said anchor elements, respectively, about an axis which extends in a direction between said first and second anchor elements and permanently securable to said first and said anchor elements, respectively, and which are received in interfitting relation and rotatable with respect to each other and slidble in telescoping relation with respect to each other in said direction to enable said base element to be adjusted to fit the width of said gap and to compensate for misalignment of said anchor elements.

2. The base structure of claim 1 further comprising means biasing said base element portions apart.

3. In the base structure of claim 1, said anchor elements further characterized as being tapered in their outward extents away from the gum of said patient when they are mounted on said first and second teeth, said first and second base element portions being configured to receive said first and second anchor elements, respectively, in snug interfitting relation when said base element is aligned with said gap and advanced toward said gum.

4. In the base structure of claim 1 said first base element portion having an aperture therein which extends in said direction between said anchor elements, said second base element portion comprising a pin which is slidably received in said aperture to enable said base element to be adjusted.

5. The base structure of claim 4 further comprising spring means received in said aperture and engaging said pin to bias said first and second base element portions apart.

6. In the base structure of claim 1 said first and second base element portions defining a tooth-like configuration of reduced dimension in said base element.

7. The base structure of claim 1 in combination with an outer shell, said base element portions being secured with respect to each other and being secured to said anchor elements, said outer shell having a tooth-like outer configuration and being received and secured on said base element.

8. A method of securing and forming a dental prosthesis in a gap between spaced first and second teeth in the mouth of a patient comprising:

a. securing first and second anchor elements to said first and second teeth, respectively, in said gap;

b. assembling a base element in said gap, said base element comprising first and second base element portions which are receivable and securable in interfitting relation with said first and second anchor elements, respectively, so that they are nonrotatable relative to said anchor elements, respectively, about an axis which extends in a direction between said first and second anchor elements and which are received in interfitting relation and rotatable with respect to each other and slidable in telescoping relation with respect to each other in said direction to enable said base element to be adjusted to fit the width of said gap;

c. securing said first and second base element portions in fixed relation with respect to each other;

d. forming an outer shell having a tooth-like outer configuration on said base element; and e. securing said base element with said outer casing thereon to said anchor elements.

9. In the method of claim 8 said base structure further comprising means biasing said first and second base element portions apart.

10. In the method of claim 9 said anchor elements being tapered in their outward extents away from the gum of said patient, said first and second base element portions being configured to receive said first and second anchor elements, respectively, in snug interfitting relation when said base element is aligned with said gap and advanced toward said gum, said assembling step being carried out by aligning said base element with said gap and advancing it toward said gum so that said anchor elements are received in snug interfitting relation with said base element.

*11. In a base structure for a dental prosthesis wherein the base structure is of a type which is permanently securable in a gap between spaced first and second teeth in the mouth of a patient and comprises a base element receivable in said gap and first and second securing means for securing said base element to said first and second teeth, respectively, to retain said base element in a position wherein it extends therebetween, the improvement comprising said base element comprising first and second base element portions which are securable to said first and second teeth, respectively, with said first and second securing means, respectively, so that they are mountable relative to said first and second teeth, respectively, about an axis which extends in a direction between said first and second teeth, said first and second base element portions being received in interfitting relation and being slidable in telescoping relation with respect to each other in said direction to enable said base element to be adjusted to fit the width of said gap, said first and second base element portions also being rotatable with respect to each other about said axis to compensate for misalignment of said first and second securing means.*

*12. The base structure of claim 11 further comprising means biasing said base element portions apart.*

*13. In the base structure of claim 11, said first base element portion having an aperture therein which extends in said direction between said teeth, said second base element portion comprising a pin which is slidably received in said aperture to enable said base element to be adjusted.*

*14. The base structure of claim 13 further comprising biasing means received in said aperture and engaging said pin to bias said first and second base element portions apart.*

*15. In the base structure of claim 11, said first and second base element portions defining a tooth-like configuration of reduced dimension in said base element.*

*16. The base structure of claim 11 in combination with an outer shell, said first and second base element portions being secured to each other, said outer shell having a tooth-like configuration and being received and secured on said base element.*

* * * * *